(12) United States Patent
Allen et al.

(10) Patent No.: US 12,208,258 B2
(45) Date of Patent: Jan. 28, 2025

(54) ELECTRICAL APPARATUS AND METHODS FOR AN EYE

(71) Applicant: THE BIONICS INSTITUTE OF AUSTRALIA, East Melbourne (AU)

(72) Inventors: Penelope Jayne Allen, East Melbourne (AU); David Anthony Xeiss Nayagam, East Melbourne (AU); Owen Burns, East Melbourne (AU); Christopher Edward Williams, East Melbourne (AU); Joel Villalobos, East Melbourne (AU)

(73) Assignee: THE BIONICS INSTITUTE OF AUSTRALIA, East Melbourne (AU)

( * ) Notice: Subject to any disclaimer, the term of this patent is extended or adjusted under 35 U.S.C. 154(b) by 648 days.

(21) Appl. No.: 17/436,311

(22) PCT Filed: Mar. 6, 2020

(86) PCT No.: PCT/AU2020/050213
§ 371 (c)(1),
(2) Date: Sep. 3, 2021

(87) PCT Pub. No.: WO2020/176948
PCT Pub. Date: Sep. 10, 2020

(65) Prior Publication Data
US 2022/0176104 A1 Jun. 9, 2022

(30) Foreign Application Priority Data
Mar. 6, 2019 (AU) .............................. 2019900739

(51) Int. Cl.
*A61N 1/05* (2006.01)
*A61N 1/36* (2006.01)
*A61N 1/375* (2006.01)

(52) U.S. Cl.
CPC ....... *A61N 1/0543* (2013.01); *A61N 1/36046* (2013.01); *A61N 1/375* (2013.01)

(58) Field of Classification Search
CPC .. A61N 1/0543; A61N 1/36046; A61N 1/375; A61B 5/065; A61B 5/398;
(Continued)

(56) References Cited

U.S. PATENT DOCUMENTS

2010/0198299 A1 8/2010 Shodo et al.
2012/0245449 A1* 9/2012 Williams ........... A61N 1/36046
607/116
(Continued)

FOREIGN PATENT DOCUMENTS

AU 2013202691 A1 5/2013
WO WO-2011022773 A1 3/2011
(Continued)

OTHER PUBLICATIONS

International Search Report issued in PCT Patent Application No. PCT/AU2020/050213 mailed on Jun. 11, 2020.
(Continued)

*Primary Examiner* — Eugene T Wu
(74) *Attorney, Agent, or Firm* — MARSHALL, GERSTEIN & BORUN LLP

(57) ABSTRACT

Disclosed is electrical apparatus for stimulating and/or monitoring an eye of a patient, comprising an implantable electrode device and a lead extending outwardly from the implantable device, the lead including a section that locates externally to the eye having at least one pre-formed bend. Also disclosed is a lead connected to an implantable electrode device, the lead having one or more stripes that extend along at least a portion of the lead. Also disclosed is an implantable device having a substrate and at least one electrode, the electrode having at least one aperture through (Continued)

which material of the substrate extends to anchor the electrode to the substrate. Other disclosed features relate to a foldable anchor device, a curved electrode substrate and depth markers, for example.

18 Claims, 9 Drawing Sheets

(58) Field of Classification Search
CPC .............. A61B 5/6821; A61B 2560/04; A61B 2562/04; A61B 2562/046; A61B 2562/164; A61B 2562/222; A61B 2560/0276; A61B 2562/043
See application file for complete search history.

(56) References Cited

U.S. PATENT DOCUMENTS

| 2015/0251002 | A1* | 9/2015 | Williams | ............. | A61B 5/6821 |
| | | | | | 607/54 |
| 2017/0165476 | A1* | 6/2017 | Greenberg | ......... | A61N 1/36046 |

FOREIGN PATENT DOCUMENTS

| WO | WO-2014032096 A1 | 3/2014 |
| WO | WO-2017/210730 A1 | 12/2017 |

OTHER PUBLICATIONS

Written Opinion issued in PCT Patent Application No. PCT/AU2020/050213 mailed on Jun. 11, 2020.
Nayagam et al., "Chronic Electrical Stimulation with a Suprachoroidal Retinal Prosthesis: A Preclinical Safety and Efficacy Study," *PLOS ONE* (2014).
Extended European Search Report issued in European Application No. 20766351.9, dated Oct. 7, 2022.

* cited by examiner

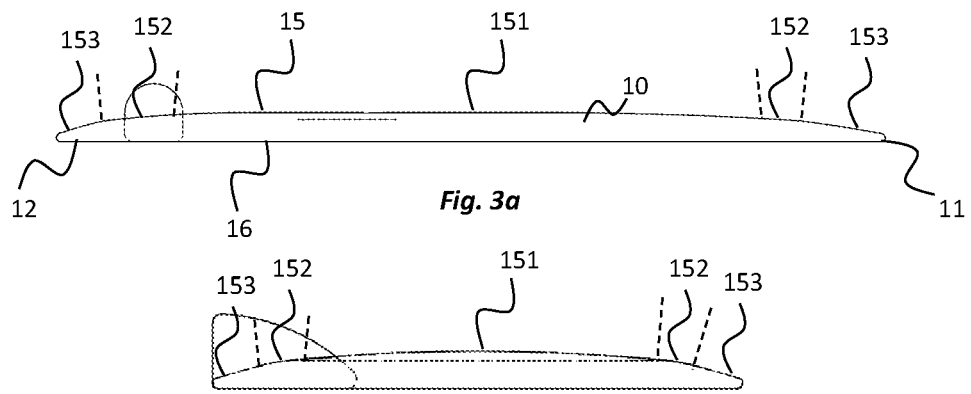
*Fig. 3a*
*Fig. 3b*
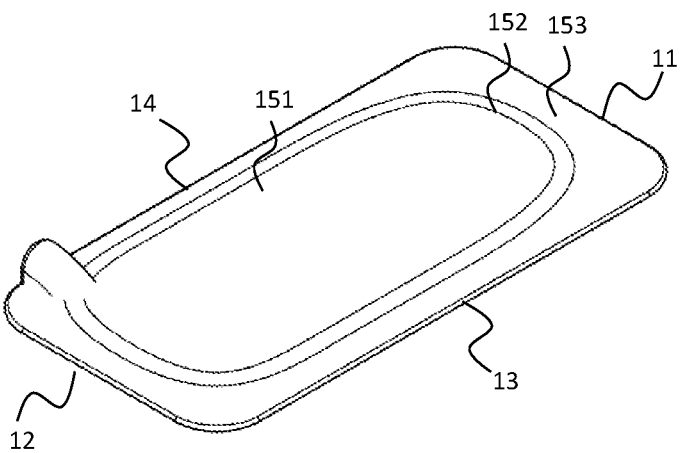
*Fig. 3c*

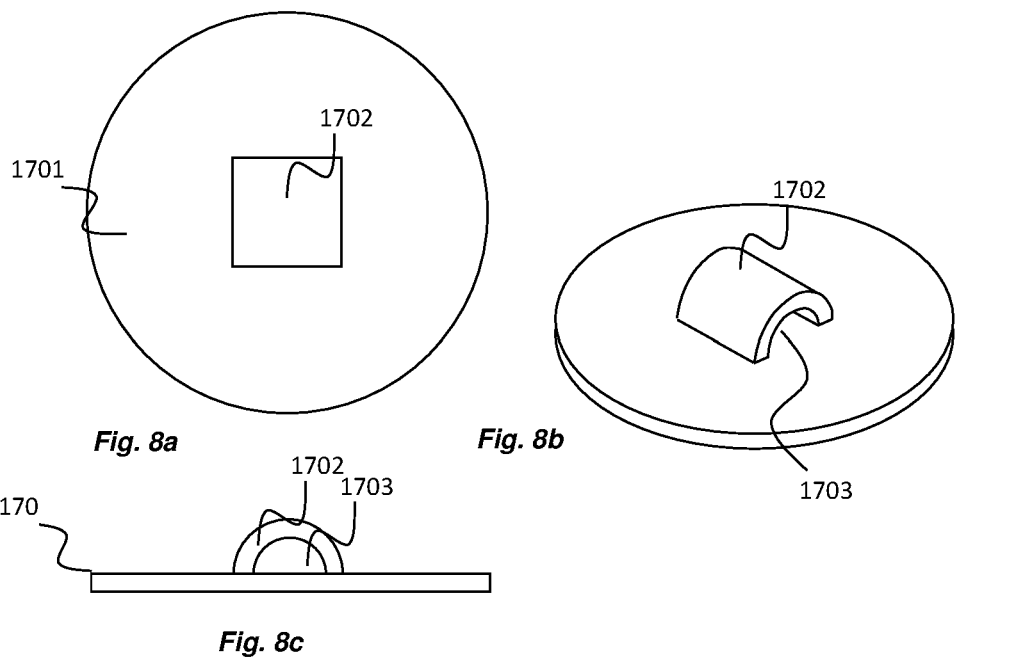
*Fig. 8a*  *Fig. 8b*  *Fig. 8c*
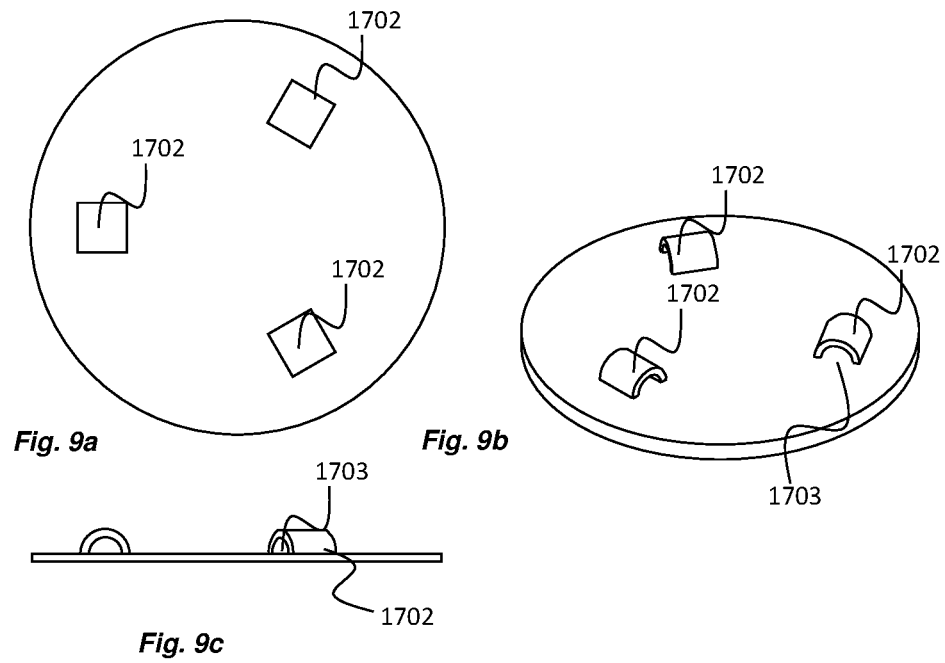
*Fig. 9a*  *Fig. 9b*  *Fig. 9c*

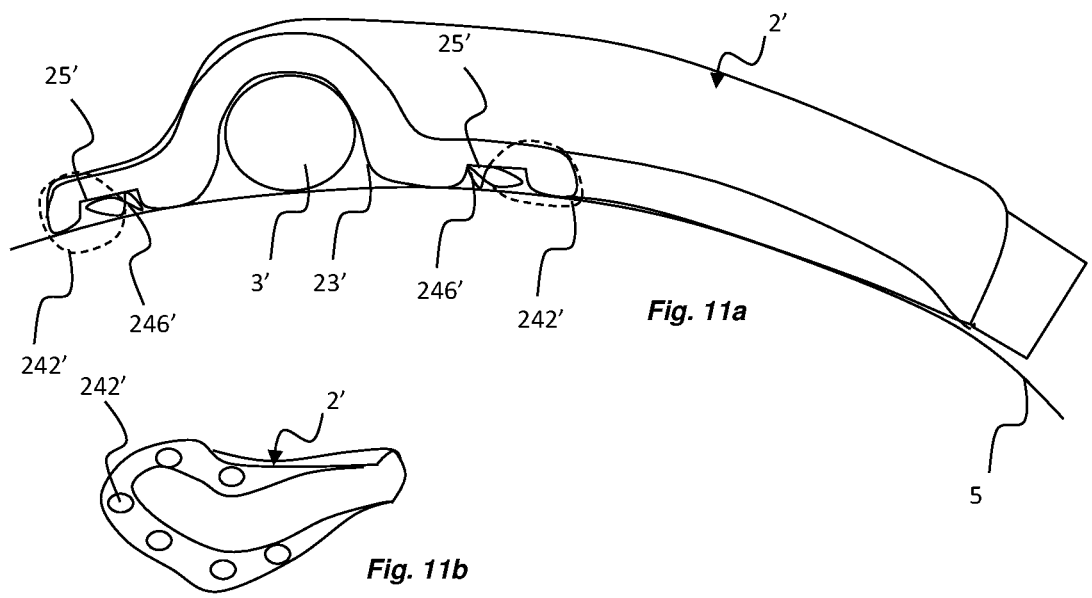
*Fig. 11a*
*Fig. 11b*
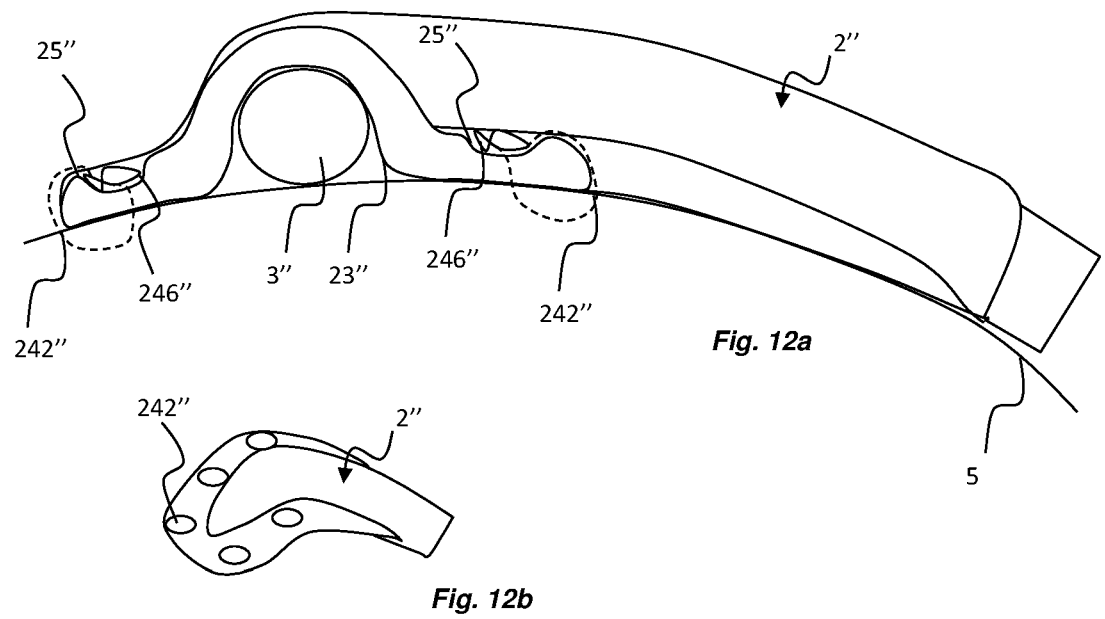
*Fig. 12a*
*Fig. 12b*

ELECTRICAL APPARATUS AND METHODS FOR AN EYE

CROSS-REFERENCE TO RELATED APPLICATION

This application claims priority to Australian provisional patent application no. 2019900739, filed 6 Mar. 2019, the entire contents of which is incorporated herein by reference.

TECHNICAL FIELD

The present patent application relates to apparatus and methods for electrically stimulating and/or monitoring electrical activity in an eye.

BACKGROUND

Electrical apparatus such as visual prostheses have been developed to restore vision within blind or partially blind patients. A visual prosthesis such as a retinal prosthesis commonly includes an implantable component having an electrode array, situated on or in a substrate, for placement in the eye on or near retinal nerve cells. Electrical signals are transmitted via the electrodes to the retinal nerve cells, triggering a perception of light within the patient's brain. The prosthesis can therefore provide the perception of vision to patients, e.g. whose retinal photoreceptors have become dysfunctional or lost.

Commonly, a visual prosthesis is used in conjunction with a video camera. A stream of images detected by the camera is converted into digital signals by an image processor and electrical signals are applied to the electrodes in accordance with the digital signals.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to one aspect of the present disclosure, there is provided electrical apparatus for stimulating and/or monitoring an eye of a patient, comprising:
  an implantable device comprising one or more electrodes, the implantable device being implantable at a stimulation and/or monitoring position between first and second tissue layers of the eye;
  a lead comprising one or more conductors connected to the electrodes, the lead extending outwardly from the implantable device;
  wherein the lead comprises first and second lead sections that locate externally to the eye when the implantable device is in the stimulation and/or monitoring position, the second lead section being configured to extend around an orbital bone adjacent the eye, and the first lead section being located between the implantable device and the second lead section;
  wherein the first lead section has at least one pre-formed bend.

The implantable device may be configured for implanting in a suprachoroidal space between the sclera and choroid layers of the eye. The first and second tissue layers may be the sclera and the choroid. However, the first and second tissue layers may be other layers, such as the choroid and the retina.

The at least one pre-formed bend may be a curved bend. The at least one pre-formed bend may provide a change in direction of the lead at the first lead section of at least 90 degrees, at least 120 degrees, at least 150 degrees or higher. The at least one pre-formed bend may provide a change in direction of about 180 degrees, for example. The at least one preformed bend may be a U-shaped bend, a double-U-shaped bend (e.g. an S-bend) or otherwise. The at least one pre-formed bend may be in only one plane or in more than one plane.

The at least one pre-formed bend may bend in a posterior direction when the implantable device is implanted in the eye. When the first lead section comprises a U-shaped bend, for example, the ends of the U-shape may therefore be located anteriorly of a middle-section, peak or apex of the U-shape.

The first lead section may be flexible and may have a length that is greater than the distance between the eye and the orbital bone. For example, the first lead section may have a length greater than the distance between a point, e.g. incision, of the eye at which the lead exits the eye, when the eye is in a forward-facing position, and a point on the orbital bone to which the lead makes contact.

During use of the electrical apparatus, the eye can rotate. To allow relatively unhindered rotation of the eye when the implantable device is implanted in the eye, the lead can exhibit a degree of flexibility and/or moveability. Without the flexibility and/or moveability of the lead, the lead can substantially hinder or prevent movement of the eye in one or more rotational directions. By providing, for example, a first lead section that is flexible and that has a length that is greater than the distance between the eye and the orbital bone, the eye may be able to move substantially in all rotational directions. As the eye rotates, depending on the direction of rotation, regions of the first lead section can bend and collect together or straighten and extend apart. By providing the first lead section with at least one pre-formed bend, the amount of force required to cause the lead to bend further or straighten can be significantly lower, reducing possible discomfort to the patient and/or possible eye damage.

The first lead section may have a circular cross-section or other cross-sectional shapes. The first lead section may have a smaller diameter than the second lead section or otherwise.

The one or more pre-formed bends of the first lead section may be formed during or subsequent to a moulding of the first lead section. The first lead section may comprise a plurality of conductive wires embedded in, or otherwise located within, a surrounding cladding layer. The cladding layer may be formed of medical grade silicone or other polymeric material, such as polyurethane, that is cured during the moulding process. The one or more bends may be formed by a post-curing technique. For example, at least one bend may be formed by rolling or holding the first lead section about a curved or angled surface while subjecting the first lead section to heating for a period of time. The curved or angled surface may be a cylindrical or part-cylindrical surface or otherwise. The radius of the curved surface may be at least 1.5 mm, at least 2 mm, at least 2.5 mm, at least 3 mm or otherwise. The pre-formed bend may have a corresponding radius of curvature. The heating may be conducted at a temperature of greater than 100° C., greater than 110° C., greater than 120° C., greater than 130° C. or otherwise. For example, heating may be conducted at a temperature of about 135° C. The heating may be conducted for a period of time greater than about 30 minutes, greater than 60 minutes, greater than 90 minutes, or otherwise. For example, heating may be conducted for a period of time of about 120 minutes.

The second lead section may comprise a reinforcement device that is adapted to be positioned at or adjacent an orbital bone. The reinforcement device may have a first end and a second end and may be elongated between the first end and the second end. The reinforcement device may be or provide a thickening of the second lead section. The reinforcement may be adapted to be positioned at or adjacent the orbital bone. The reinforcement device may be attached to the orbital bone. For example, the reinforcement device may be located in a notch formed in the orbital bone to assist with attachment to the orbital bone. The notch may include a recessed groove to receive the reinforcement device and an access opening through which the reinforcement device is locatable in the recessed groove. The access opening may be narrower than the recessed groove. The reinforcement device may be squeezed through the access opening into the recessed groove where it remains substantially trapped in position at the orbital bone.

The point at which the lead extends around the orbital bone, e.g. the point at which the notch is located, may be higher than, lower than, or level with a transverse plane extending through the centre of the eye. In a posterior direction, the notch (e.g. the groove) may be angled inferiorly or superiorly, e.g. angled superiorly by about 15 degrees.

The reinforcement device may be formed integrally with the second lead section, e.g. by a moulding technique or otherwise, or may be a discrete component. For example, the reinforcement device may be clipped to and/or glued in position at the second lead section.

The second lead section, whether or not it is associated with a reinforcement device, can have at least one pre-formed bend. When a reinforcement device is provided, the reinforcement device may have a pre-formed bend, which creates the pre-formed bend of the second lead section when it is fixed in position at the second lead section. Nevertheless, the pre-formed bend at the second lead section may be formed using alternative techniques. For example, the pre-formed bend may be formed through a post-curing technique, e.g., in the same manner that the pre-formed bend at the first lead section is formed.

The at least one pre-formed bend of the second lead section may be configured to conform to and bend around the edge of the orbital bone (the orbital rim). The at least one pre-formed bend of the second lead section may have a sharper angle than the at least one pre-formed bend of the first lead section. For example, the at least one pre-formed of the first lead section may be a curved, U-shaped bend as discussed above, and the at least one pre-formed bend of the second lead section may be an angled, V-shaped bend.

When a single pre-formed bend is provided at the first lead section, and a single pre-formed bend is provided at the second lead section, the bends may in combination provide the lead with an S-shaped configuration or a 2-shaped configuration (i.e. it may be shaped substantially like the number 2). The bends at the first and second lead sections may therefore bend in opposite directions. The bend at the first lead section may bend in a posterior direction and the bend at the second lead section may bend in an anterior direction, for example.

The first lead section of the lead may comprise one or more stripes extending along at least a portion of the lead.

Indeed, according to one aspect, the present disclosure provides electrical apparatus for stimulating and/or monitoring an eye of a patient, comprising:
    an implantable device comprising one or more electrodes, the implantable device being implantable at a stimulation and/or monitoring position between first and second tissue layers of the eye; and
    a lead comprising one or more conductors connected to the electrodes, the lead extending outwardly from the implantable device;
    wherein one or more stripes extend along at least a portion of the lead.

The one or more stripes may assist with placement of the lead during implantation of the stimulation device. Specifically, the one or more stripes may provide a visual indication to a surgeon implanting the stimulation device regarding whether or not the lead is twisted. Where the lead comprises first and second sections as described above, the one or more stripes may extend along at least the first lead section. In some embodiments the one or more stripes may extend along the entire length of the lead. The one or more stripes may be formed from a layer of titanium dioxide or other material that has a contrasting colour to adjacent parts of the lead. In some embodiments, two of the stripes may be provided, each stripe being located at substantially opposite sides of the lead.

In any aspect disclosed herein, the implantable device may comprise a substrate that the one or more electrodes are located in or on. The electrodes may be at least partly embedded in the substrate. The substrate may comprise a first, non-conductive material, e.g., a medical grade polymer material such as a silicone elastomer or polyurethane. Each electrode may comprise a second, conductive material such as a metal, e.g. a noble metal such as platinum. A portion of the substrate may provide a lip around a contact surface of each electrode. The lip may cover a peripheral edge of the contact surface and leave a central region of the contact surface exposed for making electrical contact with eye tissue. The lip may help anchor the electrode to the substrate.

The substrate may be an elongate substrate having a distal end, a proximal end, a first side, a second side, and first and second opposite surfaces each extending between the distal and proximal ends and the first and second sides. The electrodes may be at least partly embedded in the substrate and exposed at one or both of the first and second surfaces, e.g. the second surface, for making electrical contact with eye tissue. In some embodiments, the electrodes may be at least partly embedded in the substrate through forming of an initially flowable substrate material around the electrodes, prior to setting of the material. In some alternative embodiments, the electrodes may be positioned on the substrate, and embedded by way of a coating provided over the electrodes. Portions of the coating overlying the electrodes may be removed (e.g., by photolithography) to expose the underlying electrodes (or portions thereof) for making electrical contact with the eye tissue. The electrodes may be evenly distributed across the substrate or located generally closer to the distal end of the substrate than the proximal end. The substrate may be configured for insertion, via an incision, distal end first, to a stimulation and/or monitoring position between the layers of the eye, e.g., the sclera and choroid layers.

According to one aspect of the present disclosure, there is provided an implantable device for stimulating and/or monitoring an eye of a patient, the implantable device comprising:
- a substrate comprising a first, non-conductive material; and
- at least one electrode comprising a second, conductive material, the at least one electrode being at least partially embedded in the first material of the substrate and comprising at least one aperture through which first material of the substrate at least partially extends to anchor the electrode to the substrate.

The first, non-conductive material may be a flowable material that is set during a manufacturing process to form the substrate. While in a flowable state, and prior to setting, the first material may flow into the at least one aperture to completely or partially fill the aperture.

The first material may be a polymeric material that is set by curing. The first material may be a medical grade polymer material such as a silicone elastomer or polyurethane, for example. The second, conductive material may be a metal, e.g. a noble metal such as platinum.

In general, polymeric materials such as silicone elastomers or polyurethane used in substrates may not form a robust bond with noble metal materials used in electrodes. It has therefore been found that metal electrodes that are embedded at or close to the surface of elastomeric substrates can be prone to disengaging the substrates, e.g. 'popping out' of recesses in the substrates. By anchoring the electrode to the substrate in the manner described above, the risk of dislocation or popping out of the electrode can be substantially reduced.

The first material of the substrate may provide all of, or least the bulk of, the substrate. The portion of the first material that extends at least partially through the aperture of the electrode may be integral and homogenous with the first material forming all of, or the bulk of, the substrate.

The at least one aperture may be a bore hole in the electrode. The at least one aperture may have first and second opposite open ends. The first material may fill, e.g. completely fill, the aperture.

The first material may extend out of the aperture via the first and second ends. At one or both of the open ends, the first material may partially extend transversely to the aperture upon extending out of the aperture, e.g. across a surface of the electrode. The first material may form a continuous loop that extends through the aperture. The continuous loop may extend through the aperture and loop around a periphery of the electrode or through another aperture in the electrode.

By providing transversely extending portions of the first material and/or the continuous loop of first material, the at least one electrode may be trapped between portions of the first material, assisting in the anchoring of the electrode.

The at least one electrode may comprise a plurality of the apertures to increase anchoring strength.

The at least one electrode may be substantially flat. The electrode may have first and second opposite surfaces. The electrode may have a circular disk shape. The first surface of the electrode may face away from the substrate and may be at least partially exposed to enable electrical contact between the first surface and tissue of the eye. The second surface of the electrode may be buried within the substrate, e.g. the first material of the substrate.

The substrate may comprise a lip of the first material that extends around the periphery of the first surface of the electrode to assist with anchoring the electrode to the substrate, while leaving a region (e.g. a central region) of the first surface exposed.

The at least one aperture may extend between the first and second opposite surfaces of the electrode. The first open end of the aperture may be at the first surface of the electrode and the second open end of the aperture may be at the second surface of the electrode. The aperture may locate adjacent a peripheral edge of the electrode. For example, the at least one aperture may be positioned within the outer 33%, 25%, 15% or 10% of a diameter of the electrode. Where a plurality of the apertures are provided, each of the apertures may locate adjacent a peripheral edge of electrode. For example, each aperture may be positioned within the outer 33%, 25%, 15% or 10% of the diameter of the electrode. The apertures may be positioned in a ring pattern adjacent the peripheral edge of the electrode. The apertures may be uniformly spaced. By providing the apertures adjacent a peripheral edge of the electrode, the first, non-conductive material may extend through the electrode only at the peripheral edge of the electrode, ensuring that a central region of the first surface of the electrode remains exposed for electrical contact with tissue. Each aperture may have a diameter that is, e.g., less than 20%, less than 15% or less than 10% of the diameter of the electrode. For example, each aperture may have a diameter of between 100 μm and 800 μm. Each aperture may be circular, although other aperture shapes can be used.

Where a lip is provided, the first material may extend from the lip through the apertures at the periphery of the electrode. The apertures may enhance the function of the lip as a means of assisting anchoring of the electrode to the substrate.

In addition to, or as an alternative to, providing one or more apertures that extend between the first and second opposite surfaces of the electrode, at least one aperture may be defined by a projection on the second surface of the electrode. First and second opposite ends of the aperture may be defined by the projection. The projection may be a loop, handle and/or hoop, the centre of which loop, handle and/or hoop provides the aperture. The projection may be formed by a strap. The projection may have a U-shape but, in combination with the second surface of the electrode, may provide a closed-loop. A plurality of projections, each defining at least one aperture, may be provided on the second surface of the electrode.

As discussed above, the second surface of the electrode may be buried within the substrate. By providing a projection at the second surface that defines the aperture, the first material of the substrate may extend through the aperture when the second surface is buried within the substrate during manufacturing of the device, e.g., while the first material of the substrate is in a flowable state as discussed above.

In apparatus of the present disclosure, an anchor device may be provided to anchor the lead at an outer surface of the eye, at or adjacent an opening in the eye, e.g. an incision, through which the lead extends. The anchor device may comprise a proximal end portion fixed to the lead and distal end portion connected to the proximal end portion. The anchor device may be releasably secured in a folded configuration. The anchor device may be adjustable from the folded configuration to an extended configuration Indeed, according to one aspect of the present disclosure there is provided electrical apparatus for stimulating and/or monitoring an eye of a patient, comprising:

an implantable device comprising one or more electrodes, the implantable device being implantable at a stimulation and/or monitoring position between first and second tissue layers of the eye; and a lead comprising one or more conductors connected to the electrodes, the lead extending outwardly from the implantable device; and an anchor device to anchor the lead at an outer surface of the eye, at or adjacent an opening in the eye through which the lead extends, the anchor device comprising a proximal end portion fixed to the lead and a distal end portion connected to the proximal end portion, the anchor device being releasably secured in a folded configuration.

Moreover, in another aspect, there is provided a method of securing a lead at an outer surface of an eye of a patient, the lead being connected to an implantable device implanted at a stimulation and/or monitoring position between first and second tissue layers of the eye, the implantable device comprising one or more electrodes, the lead extending through an opening at an outer surface of the eye;

wherein an anchor device is provided comprising a proximal end portion fixed to the lead and a distal end portion connected to the proximal end portion, the anchor device being releasably secured in a folded configuration;

the method comprising adjusting the anchor device from the folded configuration to an extended configuration by releasing the securing of the anchor device.

In the folded configuration, the anchor device may be bent double, curved or curled back on itself or otherwise. The distal end portion (e.g. a distal tip thereof) may project towards the proximal end portion. On the other hand, in the extended configuration, the distal end portion (e.g. the distal tip thereof), may project away from the proximal end portion.

The anchor device may be releasably secured in the folded configuration by releasable securing of the distal end portion to the proximal end portion. The distal end portion may be releasably secured to the proximal end portion by one or more sutures, adhesive and/or other fixation means. To adjust the anchor device from the folded configuration to the extended configuration, a surgeon may release the securing of the distal end portion to the proximal end portion by e.g., cutting or undoing the one or more sutures and/or by applying a pull force to overcome the adhesion forces.

By releasably securing the anchor device in the folded configuration, the distal end portion of the anchor device may be temporarily held away from the opening (e.g., incision) in the outer surface of the eye through which the lead exits the eye. Accordingly, the distal end portion may not block or obstruct access to the opening in the outer surface of the eye. By maintaining such access to the opening, sutures may be applied relatively easily at the opening in the outer surface of the eye, e.g. to close up the incision, and/or other treatment to be applied at or adjacent the opening. Once such steps have been completed, the securing of the distal end portion to the proximal end portion can be released, whereupon the distal end portion may automatically, or through manipulation, project away from the proximal end portion. The distal end portion may then at least partly cover the opening in the outer surface of the eye. In general, the anchor device may extend over the lead and may cover at least part of, or all of, the opening in the outer surface of the eye. The distal and/or proximal end portions of the anchor device may be secured to the outer surface of the eye using one or more sutures or other fixation means. In some embodiments, the proximal end portion may be secured to the outer surface of the eye prior to the release from the folded configuration.

In any aspects disclosed herein, when secured to the outer surface of the eye, the anchor device may provide support and stabilisation for the lead as it extends out of the opening in the outer surface of the eye. Furthermore, the anchor device may shield the opening in the outer surface of the eye. The anchor device may also serve to route the lead in an appropriate direction away from the anchor device and the eye, e.g., past extraocular muscles of the eye and towards the lateral orbital rim. To achieve this routing, the anchor device may cause the lead to follow, or assist the lead in following, a bent path. The lead may bend by, for example, 45 to 135 degrees at the anchor device. In one embodiment, the bend of the lead at the anchor device may be a substantially right-angled bend (90 degree bend). In another embodiment, the bend may be about 50 to 70 degrees, e.g. about 55 or about 60 degrees.

The anchor device may be substantially flexible. The anchor device may comprise a polymeric material such a medical grade silicone or polyurethane. The anchor device may comprise a stiffening element embedded therein such as a mesh, e.g. polyethylene terephthalate mesh (Dacron™ mesh). The anchor device may be in the form of a patch or flap. The anchor device may be planar. The anchor device may have a pre-formed shape, e.g. channel or recess, that is adapted to receive a portion of the lead when it secures the lead to the outer surface of the eye and/or to receive one or more suture knots, preventing the knots from applying pressure to or rubbing of the anchor device. For example, the anchor device may have one or more pre-formed suture knot recesses, separate to a channel or recess adapted to receive a portion of the lead. Each suture knot recess may be adapted to receive one or more respective suture knots. One or more suture knot recesses may be provided as a depressed portion on a top surface of the anchor device. Additionally or alternatively, one or more suture knot recesses may be provided on an underside of the anchor device to create a pocket between the anchor device and the outer surface of the eye. In some embodiments, suture knot recesses may be provided on both the top surface and the underside of the anchor device. During surgery, after a suture knot has been tied, the suture may be rotated to position the knot in a recess.

In any of the above aspects, the lead may travel from the implantable device, out of the opening in outer the surface of the eye, to a communications interface remote from the eye. The communications interface may comprise a wireless transmitter/receiver or comprise an electrical connector (e.g. a plug socket or "pedestal"), allowing for a wired or wireless connection between the implantable device and an electrical component such as a signal generator, signal monitor or otherwise. The communications interface may be directly connected to, or form part of, the electrical component, or may be separate from the electrical component. In one embodiment, the communications interface may comprise a connection point between the conductors and a signal generator such as an implantable signal generator. The communications interface may be attached to, or wholly or partially implanted in, the side of the patient's head, or at another part of the patient's anatomy.

The conductors that extend from the one or more electrodes in the substrate, through the lead and/or other parts described herein, may have a helical configuration or a wavy shape. Accordingly, upon flexing of the apparatus, the conductors may expand or contract in length as necessary, avoiding damage to parts of the apparatus including the conductors themselves.

In aspects and embodiments of the present disclosure, the substrate of the implantable device may have a first surface that is curved and the degree of curvature of the first surface may increase in the longitudinal direction of the substrate from a central region of the substrate at least towards the distal end of the substrate. Moreover, in the width direction of the substrate, the first surface may be curved and the degree of curvature of the first surface may increase in the width direction from a central region of the substrate at least towards one of the first and second sides of the substrate.

Indeed, according to one aspect of the present disclosure, there is provided an implantable device for stimulating and/or monitoring an eye of a patient, the implantable device comprising:
  an elongate substrate having a distal end, a proximal end, a first side, a second side, a first surface and a second surface, the first and second surfaces each extending on opposite sides of the substrate between the distal and proximal ends and the first and second sides, a longitudinal direction of the substrate extending between the distal and proximal ends of the substrate and a width direction of the substrate extending between the first and second sides of the substrate;
  one or more electrodes located at or adjacent the distal end of the substrate;
  wherein the distal end of the substrate is configured for insertion, via an incision, to a stimulation and/or monitoring position between first and second tissue layers of the eye; and wherein:
  in the longitudinal direction of the substrate, the first surface is curved and the degree of curvature of the first surface increases in the longitudinal direction from a central region of the substrate at least towards the distal end of the substrate; and/or
  in the width direction of the substrate, the first surface is curved and the degree of curvature of the first surface increases in the width direction from a central region of the substrate at least towards one of the first and second sides of the substrate.

In one embodiment, the degree of curvature of the first surface increases in the longitudinal direction from the central region of the substrate towards both the distal and proximal ends of the substrate.

In one embodiment, the degree of curvature of the first surface increases in the width direction from the central region of the substrate towards both the first and second sides of the substrate.

The increase in curvature may be a continuous increase in curvature or a stepped increase in curvature. For example, the first surface in the longitudinal direction and/or the width direction may have different regions, each region having a constant radius of curvature, but with the radius of curvature changing from one region to the next.

The curvature at any one or more of the curved regions of the substrate may be part-spherical. The curvature at the central region of the substrate may be part-spherical and may substantially follow the spherical curvature of the eye.

The first and second tissue layers may be the sclera and the choroid of the eye, respectively. The first surface may be configured to lie against the inside of the sclera layer. The relatively low curvature of the first surface at the central region may reduce the amount of static pressure against the sclera. Nevertheless, the relatively high curvature of the first surface towards the ends and/or sides of the substrate may assist in the insertion of the substrate between the first and second tissue layers of the eye. The substrate may be pushed into place between the first and second tissue layers, causing separation of the first and second tissue layers. The relatively high curvature may assist in separating the first and second tissue layers. In general, the curvature of the substrate may ease surgical placement and forces. Moreover, the curvature may help support the incision in the eye through which the implantable device is implanted in the eye.

The curvature of the substrate may be such that the substrate tapers in thickness from a central region towards the ends and/or sides of the substrate. In general, in any aspects and embodiments disclosed herein, the substrate may taper in thickness from a central region towards the ends and/or sides of the substrate.

Where implantable devices of the present disclosure include a plurality of electrodes used to electrically stimulate the eye, in some embodiments electrical current may be applied to a plurality of the electrodes simultaneously. For example, the electrodes may be configured in an array that includes one or more groups of electrodes, e.g. electrodes grouped in lines or grouped in other arrangements. Electrical current may be applied simultaneously to electrodes of the group. The group of electrodes may include at least 2 electrodes, at least 3 electrodes or at least 4 electrodes, for example. The electrodes of the group may be electrically addressed in parallel or may be ganged together.

The simultaneous addressing of electrodes may provide an increased penetration of the electric field in eye tissue, leading to better efficacy. Moreover, reduced power consumption may be achieved as a result of lower impedances and lower charge required per electrode.

In any of the aspects described herein, the substrate of the implantable device may include one or more navigation markers to assist in the implantation of the implantable device. The navigation markers can serve as an indicator of the depth of insertion of the implantable device through an incision in the eye and/or as an indicator of the orientation of the implantable device relative to the incision.

Indeed, according to one aspect of the present disclosure, there is provided an implantable device for stimulating and/or monitoring an eye of a patient, the implantable device comprising:
  an elongate substrate having a distal end, a proximal end, a first side, a second side, a first surface and a second surface, the first and second surfaces each extending on opposite sides of the substrate between the distal and proximal ends and the first and second sides, a longitudinal direction of the substrate extending between the distal and proximal ends of the substrate and a width direction of the substrate extending between the first and second sides of the substrate;
  one or more electrodes located at or adjacent the distal end of the substrate;
  wherein the distal end of the substrate is configured for insertion, via an incision, to a stimulation and/or monitoring position between first and second tissue layers of the eye; and wherein:
  the substrate comprises one or more navigation markers, each navigation marker providing at least one of (i) an indication of the depth of insertion of the implantable device through the incision and (ii) an indication of the orientation of the implantable device relative to the incision.

At least one of the navigation markers may be a line. The line may be printed on the substrate. Alternatively, the line may be etched or moulded into the substrate, for example. The line may be provided on the first or second surface of the substrate. The line may be a straight line. The line may extend in the width direction of the substrate, perpendicular to the longitudinal direction of the substrate.

A first one of the navigation markers may be provided to mark the position at which the implantable device, when fully implanted, is to align with the incision in the eye. The first marker when positioned at the incision may indicate that the implantable device has been inserted to the full implantation depth through the incision. The first marker when positioned at the incision may indicate the orientation of the implantable device relative to the incision at the full implantation depth. Appropriate orientation at the full implantation depth may be when the first marker is positioned directly underneath and extends parallel to the incision.

A second one of the navigation markers may be provided to indicate that the implantable device has been inserted to a predetermined intermediate implantation depth through the incision, e.g. at least half of the full implantation depth. The second navigation marker may be located distally of the first navigation marker (if the first navigation marker is also present). The second marker when positioned at the incision may indicate that the implantable device has been inserted to the intermediate implantation depth through the incision. The second marker when positioned at the incision may indicate the orientation of the implantable device relative to the incision at the intermediate implantation depth. Appropriate orientation at the intermediate implantation depth may be when the second marker is positioned directly underneath and extends parallel to the incision.

Additional markers, e.g. lines, may be provided to provide additional indications of the depth of insertion of the implantable device and/or to ensure suitable orientation of the implantable device at those different depths.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

By way of example only, embodiments of the present disclosure are now described with reference to the accompanying Figures in which:

FIGS. 3a, 3b and 3c show side, end and perspective views, respectively, of the substrate of the implantable device of FIG. 1;

FIGS. 8a, 8b and 8c, show top, oblique and side views, respectively, of an alternative electrode for use in an implantable device according to an embodiment of the present disclosure;

FIGS. 9a, 9b and 9c, show top, oblique and side views, respectively, of another alternative electrode for use in an implantable device according to an embodiment of the present disclosure;

FIGS. 11a and 11b show, respectively, a cross-sectional view and an oblique bottom view of an anchor device according to an embodiment of the present disclosure; and FIGS. 12a and 12b show, respectively, a cross-sectional view and an oblique top view of an anchor device according to another embodiment of the present disclosure.

DETAILED DESCRIPTION OF EMBODIMENTS

Embodiments of the present disclosure relate to electrical apparatus for applying stimulation to any eye of a patient and/or monitoring the eye of the patient. The electrical apparatus may provide a "visual prosthesis apparatus" for improving a patient's vision (or at least giving improved "perception" of vision), and will be understood to include devices otherwise known as bionic eyes, artificial eyes, retinal prostheses and retinal stimulators or similar. However, features of the present disclosure may be useable with any type of device implanted in the eye, whether for sight restoration or otherwise, or with entirely different types of implantable devices, including devices adapted to stimulate or monitor brain activity. In general, monitoring as described herein may include, for example, measuring of a signal, e.g. from an eye, recording of signal data, processing of signal data and/or analysing of the signal data.

Figure 1:
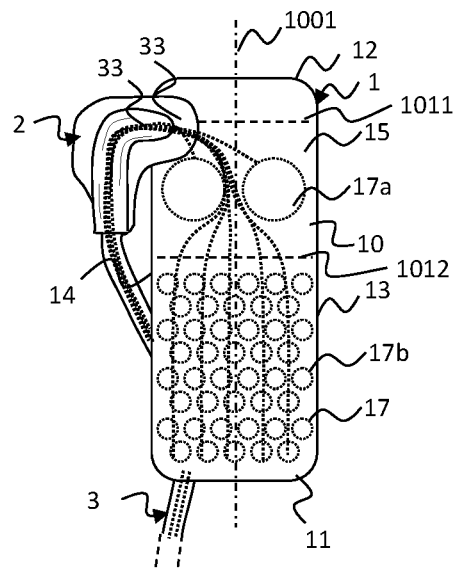
FIG. 1 shows a top view of electrical apparatus, including an implantable device for implanting in an eye, a lead and an anchor device, according to an embodiment of the present disclosure.

FIG. 1 shows a top view of electrical apparatus according to an embodiment of the present disclosure, the apparatus including an implantable device 1, an anchor device 2 and a lead 3.

The implantable device has a flexible substrate 10 with a distal end 11, a proximal end 12, a first side 13, and a second side 14. The substrate 10, when viewed from above, is substantially rectangular, with curved corners to minimise surgical trauma. The longitudinal direction (length) of the substrate extends between the distal and proximal ends 11, 12 and the transverse direction (width) of the substrate extends between the first and second sides 13, 14. The substrate 10 includes first and second opposite surfaces 15, 16 that each extend between the distal and proximal ends 11, 12 and between the first and second sides 13, 14 (see also FIG. 3a). Electrodes 17 are partially embedded in the substrate, which electrodes 17 are used to apply electrical current to tissue of the eye for the purposes of eliciting a visual percept to a subject, and/or are used to monitor properties of the eye by receiving electrical current from tissue of the eye. In this embodiment, 44 electrodes 17 are provided, the electrodes being arranged in a staggered pattern with electrodes 17 offset in rows extending in the longitudinal direction of the substrate but aligned in the transverse direction of the substrate. The electrodes 17 are exposed at the second surface 16 of the substrate.

The length of the substrate 10 is between about 16 mm and 20 mm, e.g. about 17 mm, 18 mm or 19 mm, although other lengths are possible. The width of the substrate 10 is between about 6 and 10 mm, e.g. about 8 mm, although other widths are possible. The electrodes 17 are disc-shaped electrodes with circular peripheries, although other shapes are possible. The diameters of the electrodes 17 are between about 0.4 mm and 2.5 mm, e.g., about 1.05 mm in this embodiment for stimulation electrodes 17b and about 2.1 mm for current return electrodes 17a (i.e. having a first surface area of about 0.13 mm$^2$ and 4.91 mm$^2$, i.e. about 0.87 mm$^2$). However, as discussed in more detail below, a lip 101 surrounds the electrodes 17 such that only a portion of each electrode, e.g., having a diameter of about 1.00 mm (i.e., an area of about 0.79 mm$^2$) for the stimulation electrodes 17b and 2.0 mm (i.e., an area of about 3.14 mm$^2$) for the current return electrodes 17a, is exposed from the substrate.

In addition to covering a relatively large area of the substrate 10, the electrodes 17 are sized and distributed to retain flexibility of the implantable device 1.

Each electrode 17 is connected to one or more separate electrical conductors 33, e.g., biocompatible metal wires such as platinum wires. The conductors 33 extend through the substrate, and extend out of the substrate and through the lead 3. Although only a basic representation of the conductors 33 is provided in FIG. 1, in practice the conductors 33 may be configured in a helical configuration, enabling the conductors to adjust to flexing of the implantable device 1 and/or lead 3.

The substrate 10 of the implantable device includes one or more navigation markers 1011, 1012 to assist in the implantation of the implantable device 1. The navigation markers 1011, 1012 can serve as an indicator of the depth of insertion of the implantable device 1 through an incision in the eye and/or as an indicator of the orientation of the implantable device 1 relative to the incision. In this embodiment, at least two navigation markers 1011, 1012 are provided, each on the first (rear) surface 15 of the substrate 10. In this embodiment, the navigation markers 1011, 1012 are provided in the form of lines. The lines are printed on the rear surface 15 of the substrate 10, although in alternative embodiments they may be etched or moulded into the substrate, for example. The lines 15 are straight lines that extend in a transverse (width) direction of the substrate 10, perpendicularly to the longitudinal (length) direction of the substrate 10.

A first one of the navigation markers 1011 is provided to mark the position at which the implantable device 1, when fully implanted, is to align with the incision in the eye. The first marker 1011 when positioned at the incision not only indicates that the implantable device 1 has been inserted to the full implantation depth through the incision, but also provides a means of ensuring that the implantable device 1 is oriented appropriately relative to the incision at the full implantation depth. In this embodiment, appropriate orientation at the full implantation depth is achieved when the first marker is positioned directly underneath, and extends parallel to, the incision. Notably, the first marker is positioned slightly distally of the proximal end of the substrate 10, since the implantable device 1, when fully implanted, is configured to extend either side of the incision. A major portion (distal side) of the implantable device 1 is to be located to one side of the incision with a remaining minor portion (proximal side) of the implantable device 1 being tucked to the opposite side of the incision (see e.g. FIGS. 6a to 6c). The lead 3 extends from the implantable device 1 at a position that is aligned with the first marker 1011, since it is arranged to extend from the implantable device 1 immediately through the incision.

A second one of the navigation markers 1012, which is located distally of the first navigation marker, provides an intermediate marker. It provides an indication, for example, that the implantable device 1 has been inserted to a predetermined intermediate implantation depth through the incision, e.g. at least half of the full implantation depth. Moreover, it provides an indication that the implantable device 1 is being inserted at the appropriate orientation relative to the incision at the intermediate implantation depth. In this embodiment, appropriate orientation is achieved at the intermediate implantation depth when the second marker 1012 is positioned directly underneath and extends parallel to the incision. Additional markers, e.g. lines, may be provided to provide additional indications of the depth of insertion of the implantable device and/or to ensure suitable orientation of the implantable device 1 at those different depths.

Figure 2A:
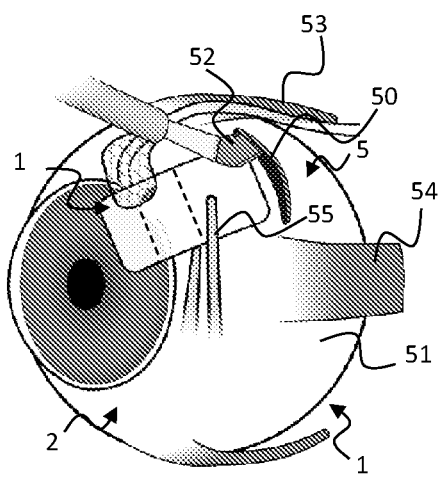
FIGS. 2a and 2b illustrate implanting of the implantable device of FIG. 1 in an eye.
Figure 2B:
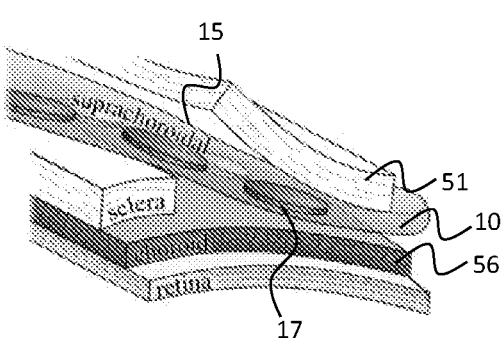

An example method of implanting the implantable device 1 in an eye 5 is now discussed with respect to FIGS. 2a and 2b. An incision 50 is made in the sclera 51 of the eye 5 with a scalpel 52, the incision 50 being slightly wider than the width of the substrate 10 of the implantable device 1. For example, the incision may have a width of about 7 to 12 mm. The incision 50 is made between the superior rectus muscle 53 and the lateral rectus muscle 54 of the eye 5. The incision is positioned about 4 to 5 mm posterior from the intramuscular septum. The distal end 11 of the substrate 10 is pushed into the incision 50, using soft-tipped forceps 53, through the sclera 51 and into a pocket between the sclera 51 and the choroid 56 (See FIG. 2b). Once fully inserted, the opening of the incision 50 is closed using sutures. When implanted, the implantable device 1 of the present embodiment is located entirely between the superior and lateral rectus muscles 53, 54 of the eye 5, in a superior anterior temporal position of the eye (e.g., in the superior anterior temporal octant of the eye). In alternative embodiments, a part of the implantable device may be located between the superior and lateral rectus muscles of the eye and a part of the implantable device may be located under one or both of the superior and lateral rectus muscles of the eye.

Stimulation provided by the implanted device 1 may restore visual function through eliciting the perception of light as a direct result of the stimulation.

By implanting the implantable device 1 suprachoroidally and at a superior anterior temporal position of the eye (e.g., in the superior anterior temporal octant of the eye), efficacious stimulation and/or monitoring of tissue of the eye can be achieved. Positioning of the implantable device 1 suprachoroidally can provide an approach that is safe and stable and requires minimally-invasive surgery.

In addition or as an alternative to providing electrical stimulation, the implantable device 1 may be used to monitor electrical properties, such as voltages, impedances or otherwise, of the eye. In one embodiment, the implantable device 1 is used to perform electroretinography monitoring (ERG).

In addition to the positioning of the implantable device 1 in the eye, safety, stability and the need for only minimally invasive surgery is provided in part through the shaping of the substrate 10 of the implantable device. A side view, an end view and an oblique view of the substrate 10 are provided in FIGS. 3a, 3b and 3c, respectively. As can be seen, the first surface 15 of the substrate is curved. When positioned suprachoroidally, the first surface 15 is designed to rest against the inner surface of the sclera 51, as illustrated in FIG. 2b.

With reference to FIG. 3a, the degree of curvature of the first surface 15 increases in the longitudinal direction from a central region 151 of the first surface 15 of the substrate 10 towards the distal end 11 of the substrate 10. The curvature of the first surface 15 also increases in the longitudinal direction from the central region 151 towards the proximal end 12 of the substrate 10. Similarly, with reference to FIG. 3b, the degree of curvature of the first surface 15 increases in the transverse direction from the central region 151 of the first surface 15 of the substrate 10 towards the first side 13 the substrate 10. The curvature the first surface 15 also increases in the longitudinal direction from the central region 151 towards the second side 14 of the substrate 10. The curvature of the first substrate 15 of the substrate 10 is such that the substrate 10 tapers in thickness from a central region of the substrate 10 towards the ends and sides of the substrate 10.

The degree of curvature of the first surface 15 changes in steps in this embodiment, although a continuous change may be provided in alternative embodiments. By increasing in steps, the first surface 15 has discrete regions, each region having a constant radius of curvature, but with the radius of curvature changing from one region to the next. In particular, at least three curved regions are provided in the present embodiment, the central region 151, a first outer region 152 and a second outer region 153, wherein the first outer region 151 is located between the central region 151 and the second outer region 152. The central region 151 has a first radius of curvature R1, the first outer region 152 has a second radius of curvature R2 and the second outer region 153 has a third radius of curvature R3, where R1>R2>R3.

The curvature of any one or more of the curved regions 151, 152, 153 can be part-spherical. In this embodiment, the curvature at the central region 151 is part-spherical and substantially follows the spherical curvature of the eye. The first surface 15 is configured to lie against the inside of the scleral. The relatively low, part-spherical curvature of at least the central region 151 of the first surface 15 reduces the amount of static pressure exerted against the sclera when the implantable device 1 is in the implantation position between the sclera and choroid. Nevertheless, the relatively high curvature of the outer regions 152, 153 of the first surface can assist in the insertion of the substrate 10 between the tissue layers of the eye. The substrate 10 can be pushed into place between the tissue layers, causing separation of the tissue layers. The relatively high curvature can assist in separating the tissue layers, essentially opening up a pocket in which the implantable device locates. The curvature of the substrate 10 may ease surgical placement and forces. Moreover, the curvature may help support the incision 50 in the eye 5 through which the implantable device 1 is implanted in the eye 5.

Figure 4A:
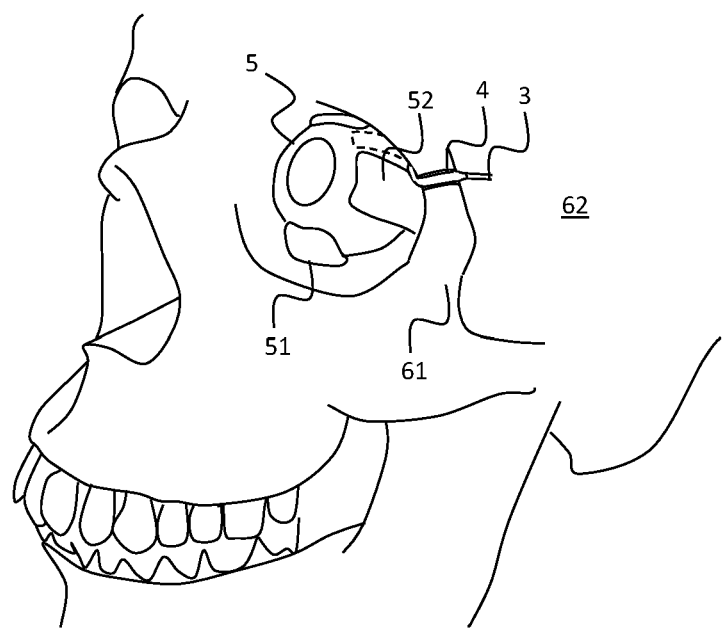
FIGS. 4a and 4b show perspective and side views, respectively, of the apparatus of FIG. 1 located relative to a skull.
Figure 4B:
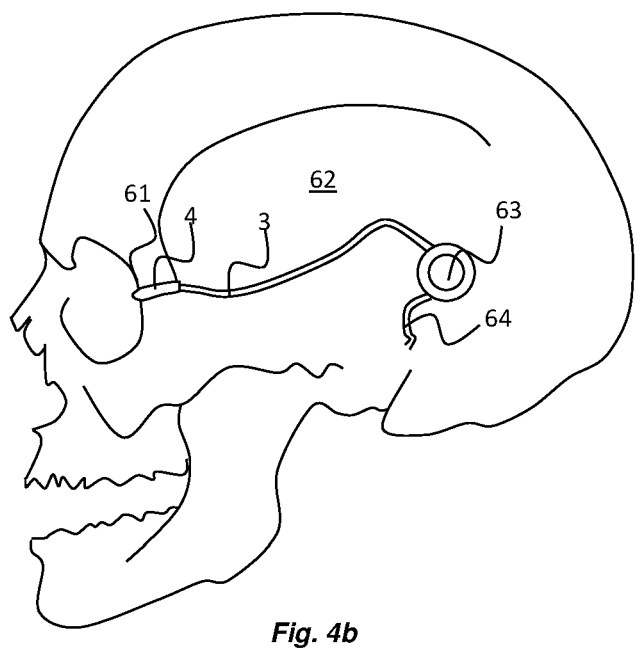

With reference to FIGS. 4a and 4b, the lead 3 is arranged to extend from the implantable device 1, through the incision in the sclera 51 of the eye 5, from the eye 5 to the adjacent orbital bone 61, around the orbital bone 61 and along the side of the patient's skull 62 to a communications interface (an implantable stimulator 63 in this embodiment). A return electrode 64 is connected to the stimulator 63. The communications interface can allow for connection between the implantable device and an electrical component such as a signal generator, signal monitor or otherwise.

Figure 5:
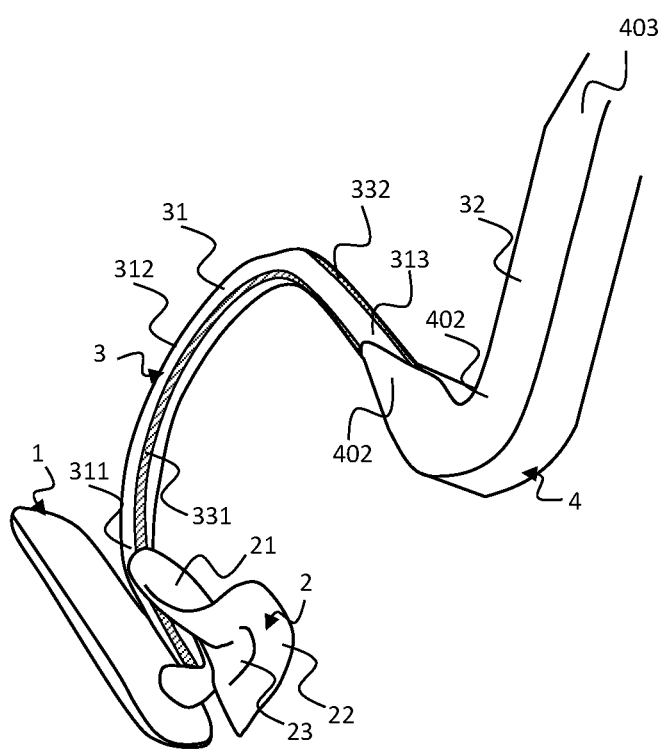
FIG. 5 shows an oblique view of the apparatus of FIG. 1, with an anchor device in a partially pre-folded configuration.

Referring also to FIG. 5, the lead 3 includes first and second lead sections 31, 32 that locate externally to the eye when the implantable device 1 is implanted in position. The second lead section 32 is configured to extend around the orbital bone 61 and the first lead section 31 is configured to locate between the implantable device 1 and the second lead section 32. The first lead section 31 has a pre-formed bend and specifically a pre-formed U-shaped bend, in this embodiment. The pre-formed bend provides a change in direction of the lead at the first lead section of about 180 degrees, although other angles may be utilised. The pre-formed bend has a radius of about 1.5 mm to 3 mm, although other radii may be utilised. Moreover, more than one pre-formed bend may be provided at the first lead section 31.

The pre-formed bend of the first lead section 31 bends in a posterior direction when the implantable device is implanted in the eye, as shown in FIG. 4a. Thus, ends 311, 313 of the U-shaped bend locate anteriorly of a middle-section 312 of the U-shape.

The first lead section 31 is flexible and has a length that is greater than the distance between the eye 5 and the orbital bone 61 and, more specifically, a length that is greater than the distance between the incision 50 of the eye 5 at which the lead 3 exits the eye, when the eye is in a forward-facing position, and a point on the orbital bone 61 to which the lead 3 makes contact as it extends around the orbital bone 61.

During use of the electrical apparatus, the eye 5 can rotate. To allow relatively unhindered rotation of the eye 5 when the implantable device 1 is implanted in the eye 5, the lead flexes and moves. Without the flexing and moving of the lead 3, the lead 3 would hinder or prevent movement of the eye 5 in one or more rotational directions. Essentially it might fix the position of the eye 5 relative to the orbital bone 61. By providing a first lead section 31 that is flexible and that has a length that is greater than the distance between the eye 5 and the orbital bone 61, the eye can move substantially in all rotational directions. As the eye rotates, depending on the direction of rotation, regions of the first lead section 31 collect together (concertina) or extend apart (straighten). By providing the first lead section 31 with the pre-formed bend, the amount of force required to cause the first lead section 31 to concertina or straighten is significantly lower, reducing discomfort to the patient and/or potential eye damage.

The pre-formed bend of the first lead section 31 in the present embodiment is formed subsequent to moulding of the first lead section 31. The first lead section 31 comprises the conductors 33 embedded in a surrounding cladding layer. The cladding layer is formed of silicone or other polymeric material, such as polyurethane, that is cured during the moulding process. The pre-formed bend is formed using a post-curing technique and specifically by rolling or holding the first lead section about a curved or angled surface while subjecting the first lead section to heating for a period of time. The curved or angled surface is at least part-cylindrical surface and has a radius of curvature of about 1.5 mm to 3 mm in this embodiment. The heating is conducted at a temperature of about 135° C. for a period of time of about 120 minutes, although other curvatures, temperatures and timings can be employed.

In the present embodiment, the second lead section 32 includes a reinforcement device 4 that provides for a thickening of the second lead section. The reinforcement device 4 directs the lead around the orbital bone 61 of the eye socket, as shown in FIGS. 4a and 4b, and provides protection for the lead and its conductors 61 against high stresses at this region. The reinforcement device 4 has a bend region 402, a first section 401 on the implantable device side of the bend region 402, and a second section 403 on the communications interface side of the bend region 402.

The reinforcement device 4 is arranged to be attached to the orbital bone 61. For example, the reinforcement device can be located in a notch formed in the orbital bone 61 to assist with attachment to the orbital bone 61. The notch can include a recessed groove to receive the reinforcement device 4 and an access opening through which the reinforcement device 4 is locatable in the recessed groove. The access opening may be narrower than the recessed groove. The reinforcement device may be squeezed through the access opening into the recessed groove where it remains substantially trapped in position at the orbital bone. The point at which the lead extends around the orbital bone 61, at which the notch is located, is higher than a transverse plane extending through the centre of the eye. In a posterior direction, the groove of the notch is angled superiorly, by about 15 degrees.

The reinforcement device 4 is formed integrally with the second lead section 32 in this embodiment, e.g. by a moulding technique or otherwise, but may be a discrete component in alternative embodiment. For example, in alternative embodiments, the reinforcement device may be clipped to and/or glued in position at the second lead section 32.

The second lead section 32 and the reinforcement device 4 at the second lead section 32 has at least one pre-formed bend configured to conform to the angle of the orbital bone 61 such as to navigate the second lead section 32 around the orbital bone 61. The pre-formed bend at the second lead section 32 is formed through a post-curing technique, e.g., in the same manner that the pre-formed bend of the first lead section 31 is formed.

The pre-formed bend of the second lead section 32 has a sharper angle than the pre-formed bend of the first lead section 31. In particular, the pre-formed bend of the second lead section 32 is a V-shaped bend. In combination, the bends at the first and second lead sections 31, 32 provide the lead 3 with an S-shaped configuration or more specifically a 2-shaped configuration (i.e. a configuration shaped substantially like the number 2). The bends at the first and second lead sections bend in opposite directions. The bend at the first lead section 31 bends in a posterior direction as described above and the bend at the second lead section 32 bends in an anterior direction.

With reference to FIG. 5, the lead 3 has one or more stripes 331, 332 extending along the lead 3. The one or more stripes 331, 332 assist with placement of the lead 3 during implantation of the implantable device 1. Specifically, the stripes 331 provide a visual indication to the surgeon implanting the device regarding whether or not the lead 3 is twisted. The one or more strips 331, 332 extend along at least the first lead section as shown in FIG. 5, although they may extend along the entire length of the lead 3. The stripes 331, 332 can be formed from a layer of titanium dioxide or other material that has a contrasting colour to adjacent parts of the lead. Two of the stripes 331, 332 can be provided, each stripe 331, 332 being located at substantially opposite sides of the lead 3.

As indicated above, the electrical apparatus includes an anchor device 2. The anchor device 2 is provided to anchor the lead 3 at the outer surface of the eye 5, at or adjacent the incision 50 in the eye 5 through which the lead 3 extends, and to route the lead 3 away from the eye. The anchor device 2 is flexible and formed of polymeric material such a medical grade silicone or polyurethane with a stiffening element embedded at one or more portions therein, such as a mesh, e.g. polyethylene terephthalate mesh (Dacron™ mesh). The anchor device 2 is in the form of a patch or flap with a preformed shape, e.g. channel 23, that is adapted to receive a portion of the lead 3 when it secures the lead 3 to the outer surface of the eye 5.

Figure 6A:
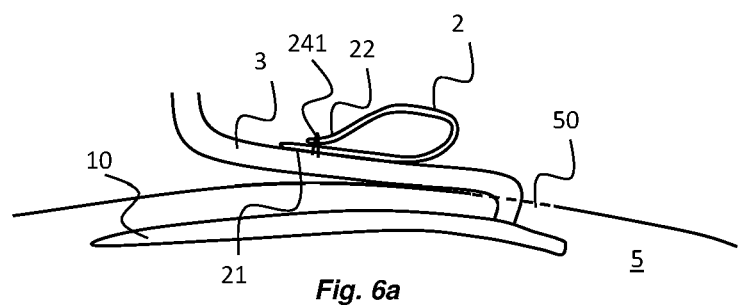
FIGS. 6a and 6b show the anchor device of FIG. 1 in a folded configuration and FIG. 6c shows the anchor device of FIG. 1 in an extended configuration.
Figure 6B:
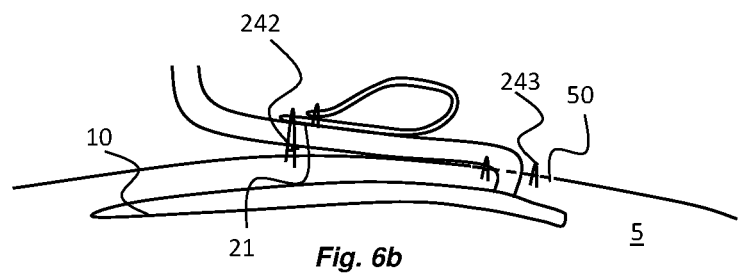
Figure 6C:
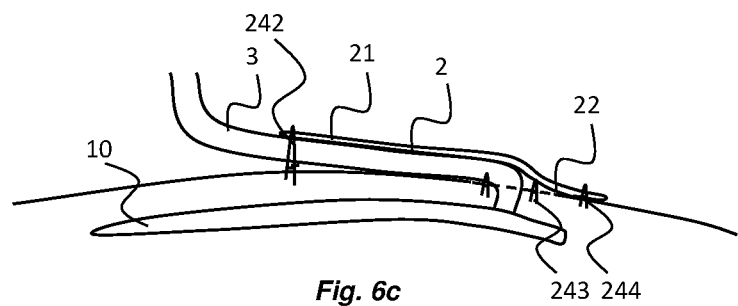

The anchor device 2 includes a proximal end portion 21 fixed to the lead 3 and a distal end portion 22 connected to the proximal end portion. Prior to implantation of the implantable device 1, e.g. during the manufacturing process, the anchor device 2 is releasably secured in a folded configuration in which the distal end portion 22 projects towards the proximal end portion 21, as illustrated in FIG. 6*a*. The releasable securing of the anchor device 2 in the folded configuration is achieved by providing at least one suture 241 to suture the distal end portion 22 to the proximal end portion 21, although other releasable fixation means may be employed such as adhesive.

While the anchor device 2 is in the folded configuration, the proximal end portion 21 may be secured to the outer surface of the eye 5, e.g., using one or more sutures 242.

By releasably securing the anchor device 2 in the folded configuration, the distal end portion 22 of the anchor device 2 can be temporarily held away from the incision 50 in the outer surface of the eye 5 through which the lead 3 exits the eye. Accordingly, the distal end portion 22 does not block or obstruct access to the incision 50 in the outer surface of the eye 5. By maintaining such access to the incision 50, sutures 243 can be applied more easily at the incision 50 in the outer surface of the eye 5, e.g. to close up the incision 50 (see FIG. 6*b*), and/or other treatment can be more easily applied at or adjacent the incision. Once such steps have been completed, the suture 241 securing the distal end portion 22 to the proximal end portion 21 can be released, whereupon the distal end portion 22 automatically, or through manipulation, projects away from the proximal end portion 21 (see FIG. 6*c*). The distal end portion 22 can then at least partly cover the incision 50 in the outer surface of the eye 5. In general, the anchor device 2 can extend over the lead 3 and cover at least part or all of the incision 50 in the outer surface of the eye 5.

The proximal and/or distal end portions 21, 22 of the anchor device 2 can be secured to the outer surface of the eye 5 using one or more sutures 242, 244 or other fixation means. In some embodiments, alternatively or additionally, one or more side portions of the anchor device 2 may be securable to the outer surface of the eye 5 using one or more sutures or other fixation means.

With reference to FIGS. 11*a*, 11*b*, 12*a* and 12*b*, any anchor device 2', 2" according to the present disclosure, whether it is folded or otherwise, may include one or more recesses 25', 25", each configured to receive a respective suture knot 246', 246" of sutures 242', 242" used to secure the device to the surface of an eye 5. The recesses 25', 25" may be discrete recesses as shown in the Figures, or otherwise connected together. In the embodiment of FIGS. 11*a* and 11*b*, for example, the recesses 25' are each provided as depressed portions on the top surface of the anchor device 2', e.g. at side portions of the anchor device 2'. In an alternative embodiment, shown in FIGS. 12*a* and 12*b*, the recesses 25" are provided on the underside of the anchor device 2", e.g. at side portions of the anchor device 2", to create pockets between the anchor device 2" and the outer surface of the eye 5. In use, once each suture 242', 242" has been tied off, the suture may be rotated to position the suture knot 246', 246" in the respective recess 25', 25". In the embodiment of FIGS. 11a and 11b, the suture knot 246' may be pulled through the material of the anchor device to access the pocket.

In general, when secured to the outer surface of the eye 5, the anchor device 2, 2', 2" provide supports and stabilisation for the lead as it extends out of the incision 50 in the outer surface of the eye 5. Furthermore, the anchor device shields the incision 50 in the outer surface of the eye 5. The anchor device 2 also serves to route the lead 3 in an appropriate direction away from the anchor device 2 and the eye 5, e.g., past extraocular muscles of the eye and towards the lateral orbital rim 61. To achieve this routing, the lead 3 at the anchor device follows a bent path.

As discussed above, the implantable device 1 according to the present disclosure includes a substrate 10 and electrodes 17 partially embedded in the substrate 10. The substrate 10 is formed primarily of a first, non-conductive material; and the electrodes are formed of a second, conductive material. As will now be described with reference to FIGS. 7a to 7d, each electrode 17 includes apertures 171 through which the first material of the substrate 10 at least partially extends to anchor the electrode 17 to the substrate 10.

Each electrode 17 is substantially flat and with a first surface 172 and an opposite second surface. Each electrode 17 has a circular disk shape. The first surface 172 of the electrode faces away from the substrate 10 and is partially exposed from the substrate 10 to enable electrical contact with tissue of the eye 5. The second surface of the electrode 17 is buried within the substrate 10 and specifically the first, non-conductive material of the substrate 10. Each aperture 171 of the electrode 17 has open ends at the first and second surfaces of the electrode 17.

In this embodiment, a plurality of the apertures 171 are provided in each electrode 17, adjacent a peripheral edge of the electrode 17. The apertures 171 are uniformly spaced and positioned in a ring pattern adjacent the peripheral edge of the electrode 17 and positioned within the outer 10 or 15% of the diameter of the electrode 17. Each aperture 171 has a diameter that is less than 15% of the diameter of the electrode 17. For example, each aperture may have a diameter of between 100 μm and 800 μm. Each aperture may be circular, although other aperture shapes can be used.

The first, non-conductive material is a flowable polymeric material such as a silicone elastomer or polyurethane that is set during the manufacturing process to form the substrate 10. While in the flowable state, and prior to setting, the first material can flow into each aperture 171 to fill the aperture, generally as represented by arrows 102 in FIG. 7d. The first material can extend out of the aperture 171 via the open ends of the aperture 171, whereupon the first material can extend transversely to the aperture 171 across surfaces of the electrode 17. The first material can form a continuous loop that extends through each aperture 171 and around a periphery of the electrode 17 and through other apertures 171. Thus, each electrode 17 is trapped between portions of the first material, assisting in the anchoring of the electrode 17 to the substrate 10.

Figure 7A:
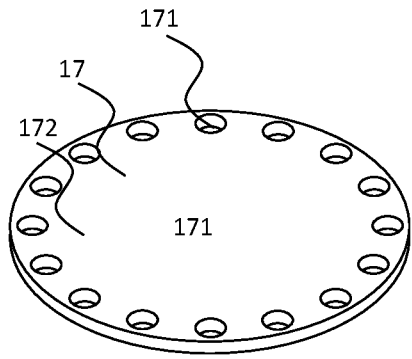
FIG. 7a shows an oblique view of an electrode of the implantable device of FIG. 1.
Figure 7B:
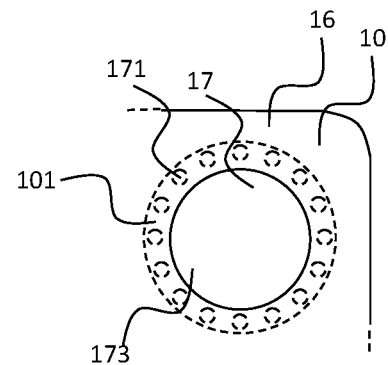
FIG. 7b shows the electrode of FIG. 7a embedded in a substrate of the implantable device of FIG. 1.
Figure 7C:
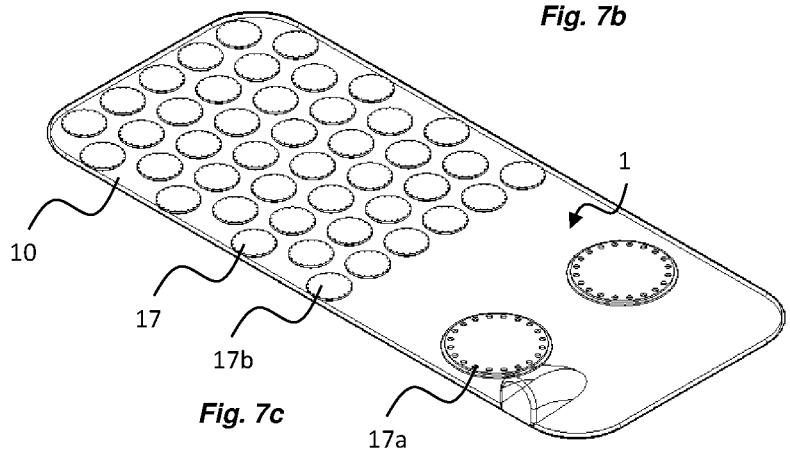
FIG. 7c shows an oblique view of the substrate with a plurality of the electrodes embedded therein.
Figure 7D:
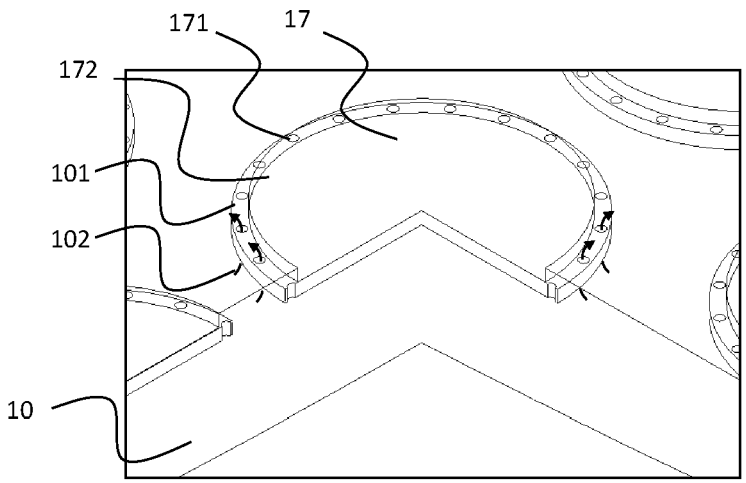
FIG. 7d shows a cross-sectional oblique view of electrodes of FIG. 7c embedded in the substrate.

As shown in FIGS. 7b and 7d, the substrate 10 provides a lip 101 of the first material that extends around the periphery of the first surface 172 of each of the electrodes 17 to assist with anchoring the electrodes 17 to the substrate, while leaving a central region 173 of the first surface 172 of each electrode 17 exposed. In this embodiment, the first material extends through the apertures 171 underneath the lip 101. Thus, the apertures 171 enhance the function of the lip 101 as a means of assisting anchoring of the electrode 17 to the substrate 10.

Figure 10:
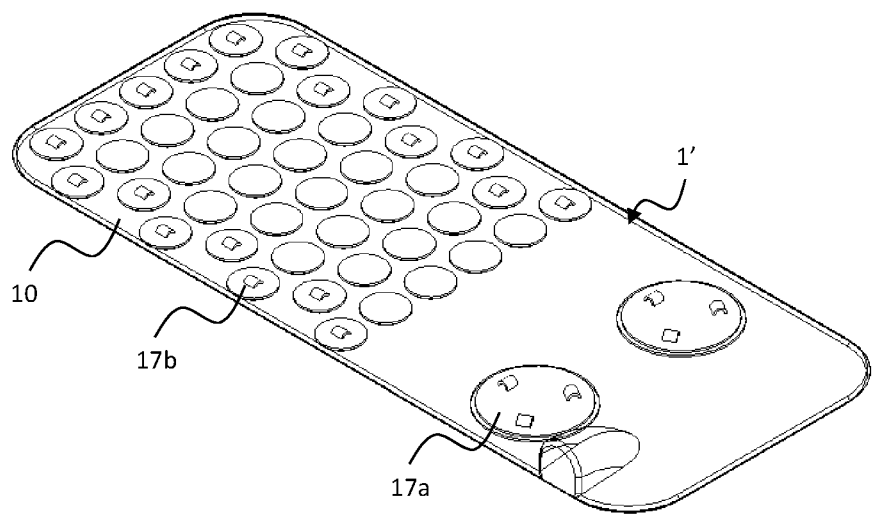
FIG. 10 shows an oblique view of an implantable device including electrodes according to FIGS. 8a to 8c and according to FIGS. 9a to 9c.

In addition to or as an alternative to providing apertures 171 that extend between the first and second opposite surfaces of the electrode 17, at least one aperture may be defined by a projection on the second surface of the electrode. For example, with reference to FIGS. 8a to 8c, the second surface 1701 of an electrode 1700 can include a projection such a loop, handle and/or hoop 1702, the centre of which provides the aperture 1703 through which first material of the substrate 10 extends. The second surface 1701 of the electrode 170 is buried within the substrate. By providing the projection 1702 at the second surface that defines the aperture 1703, the first material of the substrate can extend through the aperture 1703 when the second surface is buried within the substrate during manufacturing of the device, e.g., while the first material of the substrate is in a flowable state as discussed above. In some embodiments, as illustrated in FIGS. 9a to 9c, a plurality of the projections 1702 can be provided, each defining at least one aperture 1703. With reference to FIG. 10, the plurality of projections 1702 may be provided on relatively large electrodes, e.g. on current return electrodes 17a, whereas the single (or fewer) projection 1702 may be provided on relatively small electrodes, e.g. on stimulation electrodes 17b. As electrodes adjacent the outer edges of the substrate may be more susceptible to dislocation or popping out of the substrate, only outer electrodes 17b may be provided with the projections 1702 for the purpose of assisting anchoring of the electrodes 17b to the substrate 10.

The implantable devices of the present disclosure include a plurality of electrodes that can be used to electrically stimulate the eye. In some embodiments, electrical current may be applied to a plurality of the electrodes simultaneously. For example, two or more of the electrodes 17, shown in FIG. 1, for example, can be electrically grouped. Electrical current can be applied simultaneously to electrodes of the group. The electrodes of the group can be electrically addressed in parallel or can be ganged together. The simultaneous addressing of the electrodes 17 can provide an increased penetration of the electric field into tissue, leading to better efficacy. Moreover, reduced power consumption may be achieved as a result of lower impedances and lower charge required per electrode.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An electrical apparatus for stimulating and/or monitoring an eye of a patient, comprising:
    an implantable device comprising at least one electrode, the implantable device being implantable at a stimulation and/or monitoring position between first and second tissue layers of the eye;
    a lead comprising one or more conductors connected to the at least one electrode, the lead extending outwardly from the implantable device;
    wherein the lead comprises first and second lead sections that locate externally to the eye when the implantable device is in the stimulation and/or monitoring position, the second lead section being configured to extend around an orbital bone adjacent the eye, and the first lead section being located between the implantable device and the second lead section;

wherein the first lead section has at least one pre-formed bend;

wherein the second lead section comprises at least one pre-formed bend and wherein the at least one pre-formed bend of the second lead section is configured to conform to and bend around an edge of the orbital bone, and wherein the at least one pre-formed bend of the first lead section bends in a substantially opposite direction to the at least one pre-formed bend of the second lead section.

2. The apparatus of claim 1, wherein the at least one pre-formed bend of the first lead section provides a change in direction of the lead at the first lead section of at least 90 degrees, at least 120 degrees, or at least 150 degrees, or about 180 degrees.

3. The apparatus of claim 1, wherein the at least one preformed bend of the first lead section is a U-shaped bend.

4. The apparatus of claim 1, comprising a reinforcement device that is adapted to be positioned at or adjacent the orbital bone.

5. The apparatus of claim 4, wherein the reinforcement device provides a thickening of the second lead section.

6. The apparatus of claim 4, wherein the reinforcement device is formed integrally with the second lead section or is attached to the second lead section.

7. An electrical apparatus for stimulating and/or monitoring an eye of a patient, comprising:
an implantable device comprising at least one electrode, the implantable device being implantable at a stimulation and/or monitoring position between first and second tissue layers of the eye;
a lead comprising one or more conductors connected to the at least one electrode, the lead extending outwardly from the implantable device;
wherein the lead comprises first and second lead sections that locate externally to the eye when the implantable device is in the stimulation and/or monitoring position, the second lead section being configured to extend around an orbital bone adjacent the eye, and the first lead section being located between the implantable device and the second lead section;
wherein the first lead section has at least one pre-formed bend,
wherein the second lead section comprises at least one pre-formed bend and wherein the at least one pre-formed bend of the second lead section is configured to conform to and bend around an edge of the orbital bone, and
wherein the at least one pre-formed bend of first lead section and the at least one pre-formed bend of the second lead section provide the lead with an S-shaped configuration or a "2"-shaped configuration.

8. An electrical apparatus for stimulating and/or monitoring an eye of a patient, comprising:
an implantable device comprising at least one electrode, the implantable device being implantable at a stimulation and/or monitoring position between first and second tissue layers of the eye;
a lead comprising one or more conductors connected to the at least one electrode, the lead extending outwardly from the implantable device;
wherein the lead comprises first and second lead sections that locate externally to the eye when the implantable device is in the stimulation and/or monitoring position, the second lead section being configured to extend around an orbital bone adjacent the eye, and the first lead section being located between the implantable device and the second lead section;
wherein the first lead section has at least one pre-formed bend, and
wherein at least the first lead section of the lead comprises one or more stripes.

9. The apparatus of claim 8, comprising at least two stripes, each stripe being located at substantially opposite sides of the lead.

10. An electrical apparatus for stimulating and/or monitoring an eye of a patient, comprising:
an implantable device comprising at least one electrode, the implantable device being implantable at a stimulation and/or monitoring position between first and second tissue layers of the eye;
a lead comprising one or more conductors connected to the at least one electrode, the lead extending outwardly from the implantable device;
wherein the lead comprises first and second lead sections that locate externally to the eye when the implantable device is in the stimulation and/or monitoring position, the second lead section being configured to extend around an orbital bone adjacent the eye, and the first lead section being located between the implantable device and the second lead section;
wherein the first lead section has at least one pre-formed bend, and
wherein the implantable device comprises a substrate, the at least one electrode being at least partially embedded in the substrate, wherein the substrate comprises a first, non-conductive material, and the at least one electrode comprising a second, conductive material and wherein one or more of the electrodes comprises at least one aperture through which first material of the substrate at least partially extends to anchor the electrode to the substrate.

11. The implantable device of claim 10, wherein the first, non-conductive material is a flowable material that is set during a manufacturing process to form the substrate.

12. The implantable device of claim 10, wherein a portion of the first material that extends at least partially through the aperture of the at least one electrode is integral and homogenous with adjacent portions of the first material forming the substrate.

13. The implantable device of claim 10, wherein the at least one aperture has first and second opposite open ends, the first material extending out of the aperture via both the first and second open ends.

14. The implantable device of claim 13, wherein the first material forms a continuous loop that extends through the aperture and around a periphery of the at least one electrode or through another aperture in the at least one electrode.

15. The implantable device of claim 10, comprising a plurality of the apertures in the at least one electrode.

16. The implantable device of claim 10, wherein the at least one electrode has a first surface that faces away from the substrate and a second opposite surface buried within the substrate.

17. The implantable device of claim 16, wherein the substrate comprises a lip of the first material that extends over a periphery of the first surface of the electrode and wherein the at least one aperture is located underneath the lip.

18. The implantable device of claim 16, wherein the at least one aperture is defined by a projection on the second surface of the at least one electrode, wherein the projection is a loop, handle, and/or hoop.

\* \* \* \* \*